(12) United States Patent
Ideker et al.

(10) Patent No.: US 7,139,608 B2
(45) Date of Patent: Nov. 21, 2006

(54) PACING METHODS AND DEVICES USING FEEDBACK CONTROLLED TIMING

(75) Inventors: Raymond E. Ideker, Birmingham, AL (US); Gregory P. Walcott, Wilsonville, AL (US)

(73) Assignee: UAB Research Foundation, Birmingham, AL (US)

( * ) Notice: Subject to any disclaimer, the term of this patent is extended or adjusted under 35 U.S.C. 154(b) by 766 days.

(21) Appl. No.: 10/210,587

(22) Filed: Jul. 31, 2002

(65) Prior Publication Data

US 2004/0024421 A1 Feb. 5, 2004

(51) Int. Cl.
*A61N 1/18* (2006.01)
(52) U.S. Cl. .................................................. 607/17
(58) Field of Classification Search ............ 607/9, 607/17, 18, 19, 25
See application file for complete search history.

(56) References Cited

U.S. PATENT DOCUMENTS

| | | | | |
|---|---|---|---|---|
| 3,825,015 A | 7/1974 | Berkovits | .................... | 128/404 |
| 3,995,623 A | 12/1976 | Blake et al. | ............ | 128/2.06 E |
| 4,355,646 A | 10/1982 | Kallok et al. | ................ | 128/786 |
| 4,365,639 A | 12/1982 | Goldreyer | ................... | 128/786 |
| 4,444,195 A | 4/1984 | Gold | ........................... | 128/642 |
| 4,499,907 A | 2/1985 | Kallok et al. | ................ | 128/786 |
| 4,559,946 A | 12/1985 | Mower | .................... | 128/419 D |
| 4,567,901 A | 2/1986 | Harris | ......................... | 128/786 |
| 4,637,397 A | 1/1987 | Jones et al. | ............. | 128/419 D |
| 4,643,201 A | 2/1987 | Stokes | ......................... | 128/786 |
| 4,693,253 A | 9/1987 | Adams | .................... | 128/419 D |
| 4,708,145 A | 11/1987 | Tacker, Jr. et al. | ....... | 128/419 D |
| 4,800,883 A | 1/1989 | Winstrom | ............... | 128/419 D |
| 4,850,357 A | 7/1989 | Bach, Jr. | ................ | 128/419 D |
| 4,901,725 A | 2/1990 | Nappholz et al. | ........... | 128/419 |
| 4,928,688 A | 5/1990 | Mower | ........................ | 128/419 |
| 5,107,834 A | 4/1992 | Ideker et al. | ............ | 128/419 D |
| 5,165,403 A | 11/1992 | Mehra | ......................... | 128/419 |

(Continued)

FOREIGN PATENT DOCUMENTS

EP 0 653 223 A2 10/1994

(Continued)

OTHER PUBLICATIONS

Allessie et al., "Regional control of atrial fibrillation by rapid pacing in concious dogs," *Circulation* 1991;84:1689-1697.

(Continued)

*Primary Examiner*—Mark Bockelman
(74) *Attorney, Agent, or Firm*—Myers Bigel Sibley & Sajovec PA

(57) ABSTRACT

Methods, systems and computer program products for cardiac pacing are provided. For pacing using biventricular synchronization in a patient, a first stimulation signal is applied to a first region of a heart of the patient at a first time and a second stimulation signal applied to a second region of the heart of the patient at a second time to provide biventricular synchronization stimulation of the heart. Cardiac function of the patient associated with application of the first and the second stimulation signals is sensed and a timing relationship of the first stimulation signal to the second stimulation signal is adjusted based on the sensed cardiac function. Additionally, a cardiac timing interval, such as the A-V timing interval, may be adjusted by applying stimulation to a heart of a patient utilizing a cardiac timing interval, detecting a change in cardiac function by sensing cardiac function associated with application of the stimulation using the cardiac timing interval and adjusting the cardiac timing interval directly from the detected change in cardiac function.

83 Claims, 7 Drawing Sheets

U.S. PATENT DOCUMENTS

| | | | |
|---|---|---|---|
| 5,184,616 A | 2/1993 | Weiss | 128/419 |
| 5,201,808 A | 4/1993 | Steinhaus et al. | 128/419 |
| 5,209,229 A | 5/1993 | Gilli | 128/419 |
| 5,224,476 A | 7/1993 | Ideker et al. | 128/419 D |
| 5,230,337 A | 7/1993 | Dahl et al. | 607/5 |
| 5,235,977 A | 8/1993 | Hirschberg et al. | 607/5 |
| 5,235,978 A | 8/1993 | Hirschberg et al. | 607/5 |
| 5,251,624 A | 10/1993 | Bocek et al. | 607/6 |
| 5,267,559 A | 12/1993 | Jin et al. | 128/419 D |
| 5,269,298 A | 12/1993 | Adams et al. | 128/419 D |
| 5,269,319 A | 12/1993 | Schulte et al. | 128/786 |
| 5,282,836 A | 2/1994 | Kreyenhagen et al. | 607/4 |
| 5,292,338 A | 3/1994 | Bardy | 607/5 |
| 5,303,702 A | 4/1994 | Bonnet et al. | 607/20 |
| 5,304,139 A | 4/1994 | Adams et al. | 607/122 |
| 5,304,218 A | 4/1994 | Alferness | 607/122 |
| 5,312,444 A | 5/1994 | Bocek et al. | 607/5 |
| 5,313,953 A | 5/1994 | Yomtov et al. | 600/508 |
| 5,314,430 A | 5/1994 | Bardy | 607/5 |
| 5,324,309 A | 6/1994 | Kallok | 607/5 |
| 5,331,966 A | 7/1994 | Bennett et al. | 128/696 |
| 5,332,400 A | 7/1994 | Alferness | 607/5 |
| 5,344,430 A | 9/1994 | Berg et al. | 607/8 |
| 5,348,021 A | 9/1994 | Adams et al. | 128/708 |
| 5,350,402 A | 9/1994 | Infinger et al. | 607/5 |
| 5,366,485 A | 11/1994 | Kroll et al. | 607/5 |
| 5,366,486 A | 11/1994 | Zipes et al. | 607/5 |
| 5,387,233 A | 2/1995 | Alferness et al. | 607/126 |
| 5,395,373 A | 3/1995 | Ayers | 607/8 |
| 5,403,351 A | 4/1995 | Saksena | 607/4 |
| 5,403,354 A | 4/1995 | Adams et al. | 607/5 |
| 5,405,375 A | 4/1995 | Ayers et al. | 607/122 |
| 5,411,527 A | 5/1995 | Alt | 607/5 |
| 5,423,772 A | 6/1995 | Lurie et al. | 607/282 |
| 5,431,681 A | 7/1995 | Helland | 607/4 |
| 5,431,682 A | 7/1995 | Hedberg | 607/5 |
| 5,431,683 A | 7/1995 | Bowald et al. | 607/5 |
| 5,433,729 A | 7/1995 | Adams et al. | 607/5 |
| 5,433,730 A | 7/1995 | Alt | 607/5 |
| 5,441,519 A | 8/1995 | Sears | 607/5 |
| 5,443,491 A | 8/1995 | Snichelotto | 607/122 |
| 5,447,519 A | 9/1995 | Peterson | 607/5 |
| 5,456,706 A | 10/1995 | Pless et al. | 607/122 |
| 5,464,429 A | 11/1995 | Hedberg et al. | 607/4 |
| 5,464,432 A | 11/1995 | Infinger et al. | 607/5 |
| 5,470,348 A | 11/1995 | Neubauer et al. | 607/68 |
| 5,476,498 A | 12/1995 | Ayers | 607/122 |
| 5,476,499 A | 12/1995 | Hirschberg | 607/123 |
| 5,486,199 A | 1/1996 | Kim et al. | 607/5 |
| 5,487,753 A | 1/1996 | MacCarter et al. | 607/17 |
| 5,489,293 A | 2/1996 | Pless et al. | 607/5 |
| 5,522,853 A | 6/1996 | Kroll | 607/5 |
| 5,531,764 A | 7/1996 | Adams et al. | 607/5 |
| 5,554,176 A | 9/1996 | Maddison et al. | 607/9 |
| 5,560,369 A | 10/1996 | McClure et al. | 128/704 |
| 5,578,064 A | 11/1996 | Prutchi | 607/19 |
| 5,584,865 A | 12/1996 | Hirschberg et al. | 607/5 |
| 5,609,621 A | 3/1997 | Bonner | 607/122 |
| 5,620,471 A | 4/1997 | Duncan | 607/14 |
| 5,683,429 A | 11/1997 | Mehra | 602/14 |
| 5,697,953 A | 12/1997 | Kroll et al. | 607/5 |
| 5,718,718 A | 2/1998 | Kroll et al. | 607/5 |
| 5,800,469 A | 9/1998 | Nappholz | 607/18 |
| 5,800,470 A | 9/1998 | Stein et al. | 607/20 |
| 5,861,012 A | 1/1999 | Stroebel | 607/28 |
| 5,978,704 A | 11/1999 | Ideker et al. | 607/123 |
| 5,978,705 A | 11/1999 | KenKnight et al. | 607/5 |
| 5,987,354 A | 11/1999 | Cooper et al. | 607/5 |
| 6,002,962 A | 12/1999 | Huang et al. | 607/5 |
| 6,006,131 A | 12/1999 | Cooper et al. | 607/5 |
| 6,148,230 A | 11/2000 | KenKnight | 600/516 |
| 6,263,241 B1 | 7/2001 | Rosborough | |
| 6,275,730 B1 | 8/2001 | KenKnight et al. | 607/5 |
| 6,285,907 B1 | 9/2001 | Kramer et al. | 607/9 |
| 6,327,500 B1 | 12/2001 | Cooper et al. | 607/5 |
| 6,795,732 B1 * | 9/2004 | Stadler et al. | 607/17 |
| 2003/0204212 A1 * | 10/2003 | Burnes et al. | 607/17 |
| 2004/0019365 A1 * | 1/2004 | Ding et al. | 607/17 |

FOREIGN PATENT DOCUMENTS

| | | |
|---|---|---|
| WO | WO 98-53879 | 12/1998 |
| WO | WO 02/22207 | 3/2002 |
| WO | WO 02/051495 | 7/2002 |
| WO | WO 2004/024231 | 3/2004 |

OTHER PUBLICATIONS

Capucci et al., "Capture window in human atrial fibrillation: evidence of an excitable gap," *J Cardiovasc Electrophysiol* 1999;10:319-327.

Cooper et al., "Internal Cardioversion of Atrial Fibrillation in Sheep," Atrial Fibrillation: Mechanisms and Therapeutic Strategies, pp. 325-332 (1994).

Cooper et al., "Internal Cardioversion of Atrial Fibrillation in Sheep," Circulation, vol. 87, No. 5, May 1993, pp. 1673-1685.

Daoud et al. "Response of Type I atrial fibrillation to atrial pacing in humans," Circulation 1996;94:1036-1040.

Feeser et al., "Strength-Duration and Probability of Success Curves for Defibrillation with Biphasic Waveforms," *Circulation*, vol. 82, No. 6, Dec. 1990, pp. 2128-2141.

Garcia-Calvo et al., "The effects of selective stellate ganglion manipulation on ventricular refractoriness and excitability," PACE, 1992;15:1492-1503.

Huang et al., "Evolution of the organization of epicardial activation patterns during ventricular fibrillation," J Cardiovasc Electrophysiol, 1998;9:1291-1304.

KenKnight et al., "Regional capture of fibrillating ventricular myocardium: Evidence of an excitable gap," Circ Res 1995;77:849-855.

Kirchhof et al., "Regional entrainment of atrial fibrillation studied by high-resolution mapping in open-chest dogs," Circulation 1993;88:736-749.

Knisley et al., "Line stimulation parallel to myofibers enhances regional uniformity of transmembrane voltage changes in rabbit hearts," Circ Res 1997;81:229-241.

Kroll, Mark W., "A Minimal Model of the Monophasic Defibrillation Pulse," PACE, vol. 16, Apr. 1993, Part I, pp. 769-777.

Lewalter et al., "The Low Intensity Treadmill Exercise" Protocol for Appropriate Rate Adaptive Programming of Minute Ventilation Controlled Pacemakers, PACE, 18:1374-1387 (Jul. 1995).

Lok et al.; "Clinical Shock Tolerability and Effect of Different Right Atrial Electrode Locations on Efficacy of Low Energy Human Transvenous Atrial Defibrillation Using an Implantable Lead System", *JACC* 30:5 1324-1330 (1997).

Lüderitz et al., "Nonpharmacologic Strategies for Treating Atrial Fibrillation," The American Journal of Cardiology, vol. 77, Jan. 25, 1996, pp. 45A-52A.

Neri et al.; "Internal Cardioversion of Chronic Atrial Fibrillation in Patients", *PACE* 20 2237-2242 (1997).

Opthof et al., "Dispersion of refracteries in canine ventricular myocardium: Effects of sympathetic stimulation," Circ Res 1991;68:1204-1215.

Prof. Dr. med. Eckhard Alt; "Letters to the Editor", *PACE* 21 633-634 (1998).

Province et al., "Effect of pulse train amplitude and waveform on ability to entrain fibrillating rabbit ventricle with epicardial pacing," PACE, 22:A66 (1999) (Abstract).

Qin, Hao et al., "Recurrence Patterns After Failed Defibrillation of Spontaneous Ventricular Fibrillation During Acute Ischemia," Supplement to Journal of the American College of Cardiology, p. 3, Mar. 6, 2002, vol. 39, No. 5 Supplement A.

Qin, Hao et al., "Difibrillation Efficacy for Spontaneous and electrically-Induced Ventricular Fibrillation During Acute Ischemia," Supplement to Circulation Journal of the American Heart Association, #2125, 2000.

Qin, Hao et al., "Impact of Myocardial Ischemia and Reperfusion on Ventricular Defibrillation Patterns, Energy Requirements, and Detection of Recovery," (Circulation 2002; 105:2537) Published online before print May 6, 2002, 10.1161/01.CIR.0000016702.86180.F6.

Rogers et al., "A quantitative framework for analyzing epicardial activation patterns during ventricular fibrillation," Ann Biomed Eng 1997; 25:749-760.

Rogers et al., "Recurrent wavefront morphologies: a method for quantifying the complexity of epicardial activation patterns," Ann Biomed Eng 1997; 25:761-768.

Rollins et al., "Macintosh based programmable cardiac stimulatr," J Am Coll Cardiol, 15:261A (1990) Abstract.

Vander et al. "Human Physiology—The Mechanisms of Body Functio," pp. 230-236, Jan. 1985.

Wharton et al., "Cardiac potential and potential gradient fields generated by single, combined, and sequential shocks during ventricular defibrillation," Circulation 1992; 85:1510-1523.

PCT International Search Report, International Application No. PCT/US01/47195 dated Jul. 23, 2002.

Lammers, W. J.E.P. et al., *The use of fibrillation cycle length to determine spatial dispersion in electrophysiological properties and to characterize the underlying mechanism of fibrillation*, New Trends In Arrhythmias, vol. II, N.1, Jan.-Mar. 1986, pp. 109-112.

Laxer, Cary et al., *The Use of Computer Animation of Mapped Cardiac Potentials in Studying Electrical Conduction Properties of Arrhythmias*, IEEE, 1991, pp. 23-26.

Wolf, P. D. et al., *A 528 Channel System for the Acquisition and Display of Defibrillation and Electrocardiographic Potentials*, IEEE, 1993, pp. 125-128.

* cited by examiner

PACING METHODS AND DEVICES USING FEEDBACK CONTROLLED TIMING

FIELD OF THE INVENTION

The present invention is related to methods and apparatus for improving cardiac function in subjects.

BACKGROUND OF THE INVENTION

The heart is a muscular organ that is covered by a fibrous sac known as the pericardium. The space between the pericardium and the muscular organ is called the pericardial space. The walls of the heart are substantially formed from muscle (the myocardium) that differs from either skeletal or smooth muscle. The heart comprises atria and ventricles, each of which is composed of layers of myocardium that are formed to encase the blood-filled chambers. In operation, when the walls of a chamber contract, they come together similar to a squeezing fist. This contraction of the cardiac muscle is triggered by depolarization of the muscle membrane. To operate properly, the muscle contractions should be coordinated.

If the muscle contractions are not coordinated within the ventricles, blood may be sloshed back and forth within the ventricular cavities instead of being ejected into the aorta and pulmonary arteries. Thus, the complex muscle masses forming the ventricular pumps should contract substantially simultaneously for efficient pumping.

The heart is able to achieve this coordination because of (a) the tight junctions formed between adjacent cardiac fibers (the fibers are joined end to end at structures known as intercalated disks, which provide the points or junctions) which allow action potentials to be transmitted from one cardiac cell to another; and (b) the specialized muscle fibers in certain areas of the heart which provide the conducting system for proper excitation of the heart. The specialized fibers are in contact with fibers of the cardiac muscles to form gap junctions, which permit passage of action potentials from one cell to another. The specialized conduction system is configured, in normal operation, to provide a rapid and coordinated spread of excitation.

Cardiac muscle cells are autorhythmic, i.e., capable of spontaneous, rhythmical self-excitation. The sinoatrial (SA) node is the normal pacemaker for the entire heart or smooth muscle, and it is from this region that the excitation wave starts; it then moves or propagates through the remainder of the myocardium in a synchronized manner. The SA node region of the heart contains a small mass of specialized myocardial cells in the right atrial wall near the entrance of the superior vena cava that have a fast inherent rhythm, which allows the SA node to be the normal pacemaker. In unusual circumstances, other regions of the heart can become more excitable and provide a faster spontaneous rhythm. In this situation, this other region can become the pacemaker and the rhythm for the entire heart.

In normal operation, the cells of the SA node make contact with the surrounding atrial myocardium fibers. Thus, from the SA node, a wave of excitation spreads throughout the right atrium along the atrial myocardial cells via the gap junctions. In addition, the atrial tissue directs the impulse from the SA node directly to the left atrium, to simultaneously contract both atria.

The excitation wave then is distributed to the ventricles by way of a second small mass of specialized cells located at the base of the right atrium near the wall between the ventricles (the atrioventricular (AV) node). The AV node is configured to delay the propagation of action potentials (the wavefront) by about 0.1 second, to allow the atria to contract and empty the blood into the ventricle before ventricular contraction. The wavefront is then quickly dispersed along the specialized conducting fibers (down the interventricular septum to the ventricular free walls) and then through unspecialized (typical) myocardial fibers in the remaining myocardium.

The pumping of blood includes alternate periods of contraction and relaxation. The cardiac muscle has a relatively long refractory period (on the order of about 250 ms). This refractory period is a time during which the membrane is insensitive to stimulus (either totally unable to propagate an excitation wave or only able to do so upon exposure to an increased level of stimulation).

Heart function may be decreased in certain conditions in heart failure. In such conditions, it may be possible to increase synchronization of electrical activity that increases the muscular contraction synchronization, thereby improving cardiac function.

One approach to the improvement of cardiac function has been through biventricular synchronization utilizing a pacing device, such as a pacemaker, or other cardiac rhythm management device. Certain techniques for biventricular synchronization are described, for example, in U.S. Pat. No. 4,928,688 to Mower, the disclosure of which is incorporated herein by reference in its entirety. In general, biventricular synchronization involves application of both left ventricular and right ventricular stimulation. Initiation of the stimulation may, for example, be based on a sensed heart rate, an atrioventricular interval or the like, such as described in U.S. Pat. No. 6,285,907, the disclosure of which is incorporated herein by reference in its entirety. Typically, the left and right ventricular stimulation occur simultaneously or one of the left or right ventricular stimulation is delayed by a predefined time. For example, in an implanted device, the timing between left and right ventricular stimulation is, typically, either a fixed predefined relationship or a relationship established at the time of implantation and fixed thereafter. However, such timing may be suboptimal for a given patient or the patient's condition may change over time such that a different timing may provide better cardiac function.

SUMMARY OF THE INVENTION

Embodiments of the present invention provide methods, systems and computer program products for pacing by biventricular synchronization in a patient. In particular embodiments of the present invention, a first stimulation signal is applied to a first region of a heart of the patient at a first time and a second stimulation signal applied to a second region of the heart of the patient at a second time to provide biventricular synchronization stimulation of the heart. Cardiac function of the patient associated with application of the first and the second stimulation signals is sensed and a timing relationship of the first stimulation signal to the second stimulation signal is adjusted based on the sensed cardiac function.

In certain embodiments of the present invention, cardiac function is sensed by sensing changes in impedance. Sensing changes in impedance may be provided by measuring impedance utilizing a conductance catheter positioned on a left ventricle of the heart of the patient.

In additional embodiments of the present invention, cardiac function is sensed by measuring changes in distance and/or displacement and/or the rate of change in distance between at least two locations on the heart of the patient.

Measuring changes in distance, displacement and/or the rate of change in distance may be provided by measuring changes in distance, displacement and/or the rate of change in distance between two spatially separated sensors. For example, measurements may be made for an electrode positioned on a left ventricle and an electrode positioned within a right ventricle of the heart of the patient. Furthermore, measuring changes in distance, displacement and/or the rate of change in distance may be provided by measuring changes in distance and/or the rate of change in distance utilizing ultrasonic crystals. For example, the ultrasonic crystals may be placed on electrodes that provide the first and the second stimulation.

In still further embodiments of the present invention, cardiac function is sensed by measuring motion of a location associated with the heart of the patient. The location associated with the heart of the patient may be a left ventricle of the heart of the patient. Motion may be measured by detecting motion utilizing an accelerometer. Cardiac function may be estimated based on the detected motion. Furthermore, a derivative of the detected motion may be determined and cardiac function estimated based on the determined derivative. An integral of the detected motion may also be determined and cardiac function estimated based on the determined integral.

In additional embodiments of the present invention, the time at which the application of the first or second stimulation signals to the heart of the patient is delivered can be adjusted based on the sensed cardiac function of the patient resulting from application of the first and the second stimulation signals. The timing of the first stimulation and/or the second stimulation can be incrementally adjusted based on the sensed cardiac function adjusting the timing does not improve cardiac function. Furthermore, the timing of the first stimulation and/or the second stimulation may be adjusted until adjustment of timing of the first stimulation and/or the second stimulation does not improve cardiac function and then the timing of the other of the first stimulation and the second stimulation may be adjusted until adjustment of timing of the other of the first stimulation and the second stimulation does not improve cardiac function.

In additional embodiments, the adjustment to the stimulation timing is carried out automatically at predefined intervals. The adjustment may also be carried out if a change in cardiac function has occurred. An external signal may also initiate recalibration of biventricular synchronization timing. The sensing and adjusting may also be performed each time the first and second simulations are applied to the heart of the patient.

In still further embodiments of the present invention, applying a first stimulation to a heart of the patient at a first time, applying a second stimulation to the heart of the patient at a second time, sensing cardiac function of the patient resulting from application of the first and the second stimulation and adjusting timing of the first stimulation and/or the second stimulation based on the sensed cardiac function are carried out by an implantable pacing device.

Additionally, sensing cardiac function may also be provided by sensing the heart rate of the patient and/or sensing the timing and/or the morphology of at least one intrinsic ventricular beat of the heart of the patient.

In still further embodiments of the present invention, adjusting the timing may be provided by delaying the delivery of the second stimulation signal with respect to the first stimulation signal and/or advancing the delivery of the second stimulation signal with respect to the first stimulation signal.

In additional embodiments of the present invention, a stimulation is applied to a heart of the patient utilizing a cardiac timing interval, such as an A-V timing interval. Change in cardiac function is detected by sensing cardiac function associated with application of the stimulation using the cardiac timing interval. The cardiac timing interval is adjusted based on the detected change in cardiac function. Application of the stimulation, detecting changes in cardiac function and adjusting the cardiac timing interval may be repeated until the sensed cardiac function does not indicate an improvement in cardiac function. Furthermore, the cardiac timing interval may be adjusted by a predefined interval adjustment value that is independent of the sensed cardiac function.

Embodiments of the present invention also provide a cardiac pacing system utilizing biventricular stimulation that includes an electrode stimulation timing circuit configured to control timing between the application of stimulation to a first electrode(s) and application of stimulation to a second electrode(s) to provide biventricular synchronization stimulation of the first electrode(s) and the second electrode(s), a cardiac function sensing circuit and a feedback control circuit operatively associated with the electrode stimulation timing circuit and the cardiac function sensing circuit and configured to adjust the timing between application of stimulation to the first electrode(s) and application of stimulation to the second electrode(s) based on sensed cardiac function.

The cardiac function sensing circuit may be configured to sense changes in impedance of at least one region of the heart. For example, a conductance catheter configured to be positioned on a left ventricle of the heart of the patient may also be provided and the cardiac function sensing circuit may be operably associated with the conductance catheter.

The cardiac function sensing circuit may also be configured to measure changes in distance, displacement and/or the rate of change in distance between at least two locations on the heart of the patient. The cardiac function sensing circuit may be configured to measure changes in distance, displacement and/or the rate of change in distance between at least an electrode positioned on a left ventricle and an electrode positioned within a right ventricle of the heart. Ultrasonic crystals may be positioned on the first electrode and the second electrode and the cardiac function sensing circuit may be configured to measure changes in distance and/or the rate of change in distance utilizing the ultrasonic crystals.

The cardiac function sensing circuit may also be configured to measure motion of a location associated with the heart of the patient. For example, the location associated with the heart of the patient may be the left ventricle of the heart of the patient. The cardiac function sensing circuit may be configured to detect motion utilizing an accelerometer. The cardiac function sensing circuit may be configured to estimate cardiac function based on the detected motion. The cardiac function sensing circuit may be further configured to determine a derivative of the detected motion and estimate cardiac function based on the determined derivative. The cardiac function sensing circuit may also be configured to determine an integral of the detected motion and estimate cardiac function based on the determined integral.

In further embodiments of the present invention, the timing circuit, sensing circuit and feedback circuit are configured to repeatedly apply a first stimulation signal to a heart of the patient at a first time, apply a second stimulation signal to the heart of the patient at a second time, sense cardiac function of the patient associated with application of the first and the second stimulation signals and adjust timing of the first stimulation signal and/or the second stimulation signal based on the sensed cardiac function until adjusting timing does not improve cardiac function.

In certain embodiments of the present invention, the timing circuit, sensing circuit and feedback circuit are further configured to adjust timing of one of the first stimulation and the second stimulation until adjustment of timing of the one of the first stimulation and the second stimulation does not improve cardiac function and then adjust timing of the other of the first stimulation and the second stimulation until adjustment of timing of the other of the first stimulation and the second stimulation does not improve cardiac function.

The timing circuit, sensing circuit and feedback circuit may also be configured to repeat adjusting the timing between stimulation of the first electrode and stimulation of the second electrode after a predefined time interval has elapsed. The sensing circuit may also be configured to determine if a change in cardiac function has occurred and the timing circuit, sensing circuit and feedback circuit may be configured to adjust the timing between stimulation of the first electrode and stimulation of the second electrode if a change in cardiac function has occurred. The feedback circuit may be configured to receive an external signal initiating recalibration of biventricular synchronization timing and the timing circuit, sensing circuit and feedback circuit may be configured to adjust the timing between stimulation of the first electrode and stimulation of the second electrode responsive to receipt of the external signal.

In additional embodiments of the present invention, the sensing circuit is configured to sense cardiac function each time the first and second stimulations are applied to the heart of the patient and the feedback circuit is configured to adjust timing each time the first and second simulations are applied to the heart of the patient.

The timing circuit, sensing circuit and feedback circuit may be held in an implantable pacing device.

In certain embodiments of the present invention, the cardiac function sensing circuit is configured to sense heart rate of the patient and/or timing and/or morphology of at least one intrinsic ventricular beat of the heart of the patient.

The timing circuit may also be configured to adjust the timing between the stimulation of the first electrode and the stimulation of the second electrode utilizing variable timing adjustment intervals. The timing control circuit may adjust timing by delaying the stimulation of the second electrode with respect to the stimulation of the first electrode and/or by advancing the stimulation of the second electrode with respect to the stimulation of the first electrode. The feedback circuit may also adjust timing of stimulation of the first electrode with respect to stimulation of the second electrode proportional to the sensed cardiac function.

In other embodiments of the present invention, cardiac pacing in a patient is provided by applying stimulation to a heart of the patient utilizing an A-V timing interval, detecting a change in cardiac function by sensing cardiac function associated with application of the stimulation using the A-V timing interval and adjusting the A-V timing interval directly from the detected change in cardiac function.

In further embodiments of the present invention, a change in cardiac function is detected by sensing changes in impedance. In such embodiments, the A-V timing interval comprises adjusting the A-V timing interval directly from the sensed changes in impedance. Changes in impedance may be sensed utilizing a conductance catheter positioned proximate a left ventricle of the heart of the patient.

In additional embodiments of the present invention, a change in cardiac function is detected by measuring changes in distance and/or the rate of change in distance between at least two locations on the heart of the patient. In such embodiments, the A-V timing interval is adjusted by adjusting the A-V timing interval directly from the changes in distance and/or the rate of change in distance. Changes in distance and/or the rate of change in distance may be measured by measuring changes in distance and/or the rate of change in distance between at least an electrode positioned on a left ventricle and an electrode positioned within a right ventricle of the heart of the patient. Changes in distance and/or the rate of change in distance may also be measured by measuring changes in distance and/or the rate of change in distance utilizing ultrasonic crystals. In particular, the ultrasonic crystals may be placed on electrodes that receive the first and the second stimulation signals.

In still further embodiments of the present invention, a change in cardiac function is detected by measuring motion of a location associated with the heart of the patient. In such embodiments, the A-V timing interval is adjusted directly from the measured motion. The location associated with the heart of the patient may be a left ventricle of the heart of the patient. Furthermore, a change in cardiac function may be detected utilizing an accelerometer. Cardiac function may be estimated based on the detected motion and the A-V timing interval adjusted directly from the estimated cardiac function. Additionally, a derivative of the detected motion may be determined and cardiac function estimated based on the determined derivative. An integral of the detected motion could also be determined and cardiac function estimated based on the determined integral.

In other embodiments of the present invention, methods, systems and computer program products are provided for applying stimulation to a heart of the patient utilizing a cardiac timing interval, such as a pacing interval, A-V interval and/or interval to left and/or right ventricular stimulation, detecting a change in cardiac function by sensing cardiac function associated with application of the stimulation using the cardiac timing interval and adjusting the cardiac timing interval directly from the detected change in cardiac function are repeated until adjusting the cardiac timing interval does not improve cardiac function. Such operations may be repeated if a predefined time interval has expired. Similarly, such operations could be repeated if a change in cardiac function has occurred. Alternatively, the operations could be repeated upon receipt of an external signal initiating recalibration of the cardiac timing interval.

Additionally, in certain embodiments of the present invention, the application of stimulation to a heart of the patient utilizing an A-V timing interval, detection of a change in cardiac function by sensing cardiac function associated with application of the stimulation using the A-V timing interval and adjustment of the A-V timing interval directly from the detected change in cardiac function may be provided by an implantable pacing device.

Furthermore, detecting a change in cardiac function by sensing cardiac function may further include at least one of sensing heart rate of the patient and/or sensing timing and/or morphology of at least one intrinsic ventricular beat of the heart of the patient. The A-V timing interval may also be adjusted utilizing a variable adjustment interval. The operations of applying a stimulation, detecting change in cardiac function and adjusting the A-V timing interval may also be successively repeated utilizing finer timing adjustment intervals. Adjustment of the A-V timing interval may be provided by increasing and/or decreasing the A-V timing interval. The adjustment of the A-V timing interval may also be carried out utilizing a fixed adjustment interval.

As will be appreciated by those of skill in the art in light of the present disclosure, the present invention may be embodied as systems, methods and/or computer program products.

DESCRIPTION OF PREFERRED EMBODIMENTS

Figure 1:
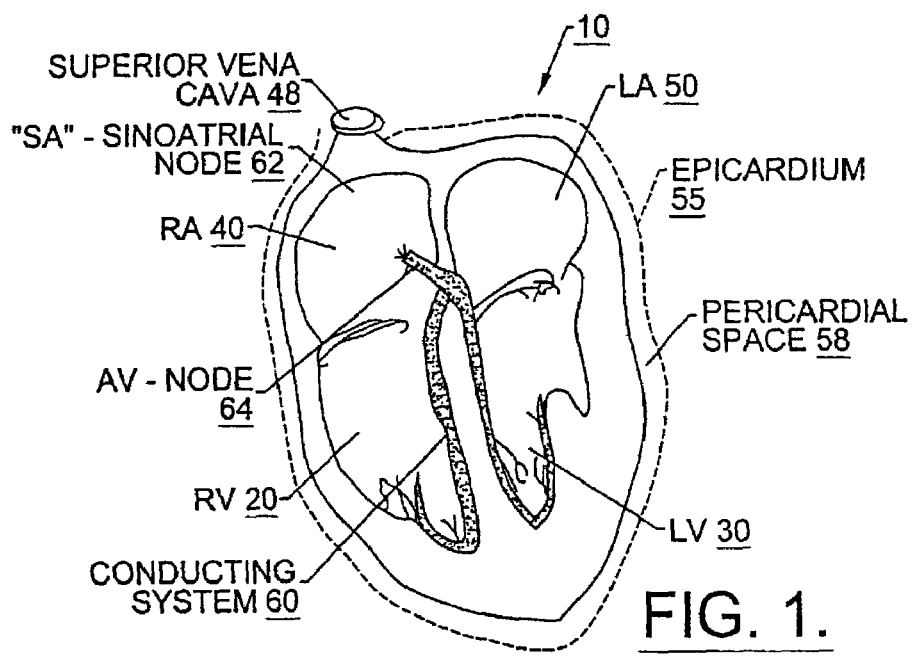
FIG. 1 is a schematic illustration of a human heart.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, layers, components, or features may be exaggerated for clarity.

The present invention may be used for pacing the heart so as to improve cardiac function. Subjects according to the present invention can be any animal subject, are preferably mammalian subjects (e.g., humans, canines, felines, bovines, caprines, ovines, equines, rodents, porcines, and/or lagomorphs), and more preferably are human subjects.

Embodiments of the present invention provide for adjusting the timing of stimulation based on measurement of cardiac function. In some embodiments of the present invention, cardiac timing, such as A-V timing, is adjusted based on whether an adjustment in the timing improves a measure of cardiac function. Conventionally, measurements of cardiac characteristics have been utilized to predict A-V timing and that predicted A-V timing utilized for cardiac pacing. See e.g., U.S. Pat. No. 6,285,907 to Kramer et al. However, according to particular embodiments of the present invention, cardiac timing, such as A-V timing, may be adjusted without the need to predict a desired timing. Such embodiments may adjust A-V timing directly based on whether changes in A-V timing improve a measurement of cardiac function. Thus, the A-V timing interval may be adjusted directly from detected changes in cardiac function. As used herein, adjusting the A-V timing interval directly from the detected change in cardiac function refers to making such adjustments without predicting a desired A-V timing.

In further embodiments of the present invention, the timing between stimulation at different stimulation sites utilized by a pacing system is adjusted based on sensed cardiac function. Such stimulation may provide biventricular synchronization to the heart. The timing of the different stimulations may be adjusted relative to a common synchronization signal, such as an atrial pulse, such that each signal is referenced to the common atrial pulse. In such cases, the timing with respect to the atrial pulse and/or the timing of the different stimulation signals relative to each other may be adjusted with reference to the atrial pulse. Such may be the case where synchronization is based on a spontaneous atrial signal. However, if atrial fibrillation is present, there may be no spontaneous atrial signal. As such, the timing of the stimulation of the different stimulation sites may be relative to each other or to an external stimulation, such as pacing signal.

To provide stimulation signals to the heart, one or more electrodes may be placed at a site such that references to an electrode herein may refer to one or more electrodes associated with a stimulation site. Accordingly, references to stimulation of an electrode or application of a stimulation signal may refer to stimulation of the one or more electrodes associated with a stimulation site. The various stimulation sites utilized may depend on the particular patient and/or pacing regime. Such sites may, for example, include those described in U.S. Pat. Nos. 4,929,688 and 6,285,907. Similarly, differing electrode configurations and locations may also be utilized with embodiments of the present invention. For example, the placement and type of electrodes may be as described in U.S. patent application Ser. No. 09/742,651 filed Dec. 21, 2000 and entitled "PACING METHODS AND DEVICES FOR TREATING CARDIAC ARRHYTHMIAS AND FIBRILLATION," the disclosure of which is incorporated herein by reference as if set forth in its entirety. Suitable commercially available electrodes may include defibrillation electrodes well known to those of skill in the art. In some embodiments, the electrodes that are adapted to reside in the heart in the vein(s) of a subject may be particularly suitable. See also, U.S. Pat. Nos. 5,107,834, 5,224,476, 5,978,704, and 6,002,962, the contents of which are hereby incorporated by reference as if recited in full herein.

The catheters or electrodes may also include sensors for measuring cardiac function. For example, a catheter may include one or more stimulation electrodes and/or sensors for sensing one or more of the onset of a treatment condition or the intrinsic cardiac cycle. See U.S. Pat. No. 5,978,704, entitled, Method and Apparatus for Treating Cardiac Arrhythmia, the contents of which are hereby incorporated by reference as if recited in full herein. Furthermore, according to embodiments of the present invention, the sensors may also include sensors for detecting indicators of cardiac function, such as, for example, measuring changes in impedance, changes in distance between electrodes and/or the rate of change of distance and/or detection of motion through, for example, use of an accelerometer. As used herein, motion refers to acceleration, velocity, displacement, integrals of acceleration, displacement and/or velocity and/or derivatives of acceleration displacement and/or velocity.

Figure 2:
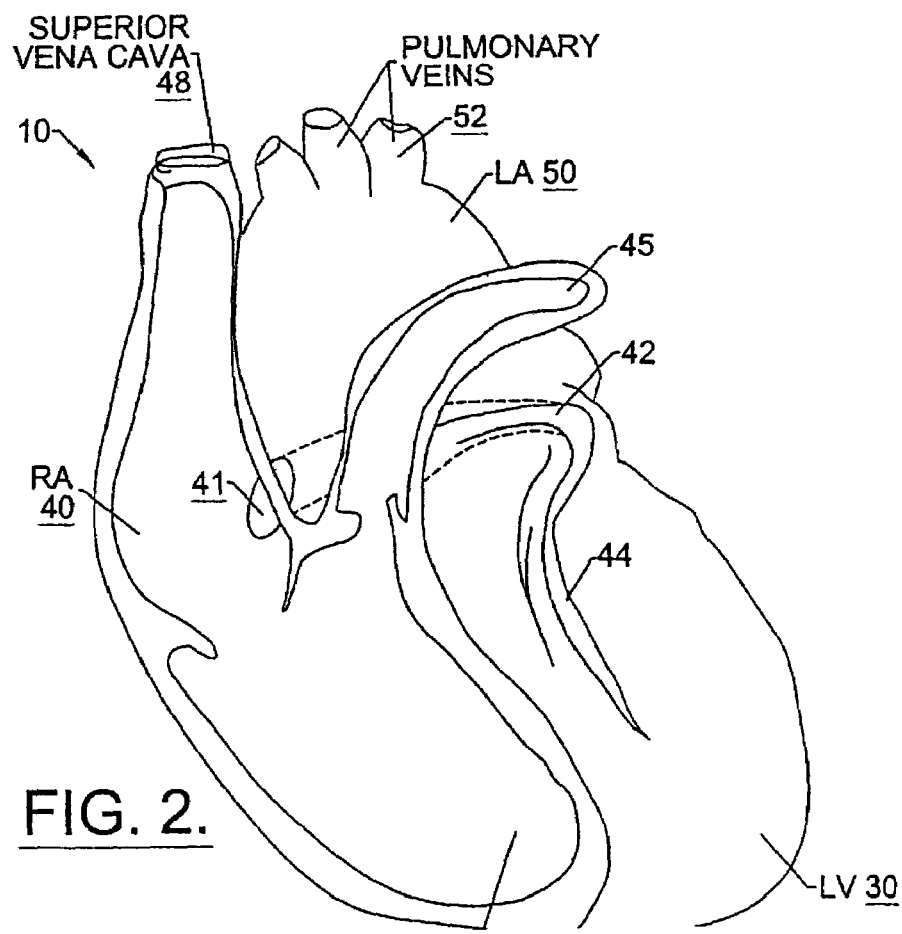
FIG. 2 is a schematic illustration of a human heart.

Anatomically, the heart includes a fibrous skeleton, valves, the trunks of the aorta, the pulmonary artery, and the muscle masses (myocardium) of the cardiac chambers (i.e., right and left atria and right and left ventricles). The schematically illustrated portions of the heart 10 shown in one or more of FIG. 1 or 2 include the right ventricle "RV" 20, the left ventricle "LV" 30, the right atrium "RA" 40 (the term "right atrium" herein including the superior vena cava and innominate vein), the left atrium "LA" 50 (and parts thereof), the superior vena cava 48, the coronary sinus "CS" 42, the great cardiac vein 44, the left pulmonary artery 45 (the term "left pulmonary artery" herein includes the main pulmonary artery and the right ventricular outflow tract), and the coronary sinus ostium or "OS" 41. FIG. 1 also illustrates the epicardium 55 (shown in dotted line) surrounding the walls of the heart (i.e., the myocardium) and the pericardial space 58 therebetween. FIG. 2 also illustrates the pulmonary veins 52 and neighboring regions. Other regions of interest may include the atrial septum, right and left atrial appendages, and the tricuspid annulus. FIG. 1 also illustrates the conducting system 60, the SA node 62 and the AV node 64.

As mentioned above, the desired localized region(s) selected for placement of the electrodes, the stimulation sites, and/or pacing the heart according to embodiments of the present invention may vary depending on the physiology or ailment of the patient. As such, the electrodes may be positioned in a number of regions and by a number of different techniques so that they are proximate to and/or in contact with the desired localized region of the myocardium. For example, the electrodes can be positioned in the natural lumens of the heart (atriums, ventricles, veins, arteries, etc.), or in the pericardial space, on the outer, inner surfaces of the cardiac walls, or within the thickness of the muscle walls. The electrodes may be positioned into the body of the subject by surgical techniques or by inserting them using locating catheters holding same, and the like. In some embodiments, certain electrodes are configured and sized such that each is able to contact the tissue at a respective stimulation or sensing site during the heartbeats. As used herein, "localized" refers to the electrical stimuli being delivered to a portion of the heart rather than to the entire heart.

Thus, as noted above, the pacing electrodes may be positioned in the pericardial space or other localized regions of the heart. For example, the pacing electrode(s) can be held on a catheter and inserted into the endocardium or threaded through the heart and inserted into the veins in the heart (threaded through the OS and looped into the veins). In some embodiments, pacing of the left atrium may be performed by locating an electrode(s) to extend in a portion of the left atrium and into the pulmonary vein(s) to help eradicate or control fibrillation activation in this region. Locating one or more electrodes in the pulmonary veins may be particularly suitable for the treatment of atrial fibrillation. Other exemplary placements are discussed below.

As described above, the driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers then travels into the atria and subsequently passing through the AV node and, after a slight delay, into the ventricles. Sensing cardiac activation or contractions while pacing can provide data to the pacing system (controller or cardiac monitor) which can be assessed to determine and adjust, as needed, a number of operational parameters such as, for example: (a) when to stop the pacing stimulation; (b) the speed or rate of the pacing stimulation (increase or decrease the pacing rate), the duration or intensity of the stimulation pulse(s); (c) whether the tissue is being successfully captured; and (d) the number of pulses/pulse trains to be relayed to the localized region.

According to embodiments of the present invention, sensed cardiac function may also be utilized to adjust the timing between stimulation of the differing regions, stimulation sites, where electrodes have been placed to provide biventricular synchronization. For example, in biventricular synchronization, measurement of cardiac function may be utilized in a feedback system to control timing between stimulation of the left ventricle and stimulation of the right ventricle.

Figure 3:
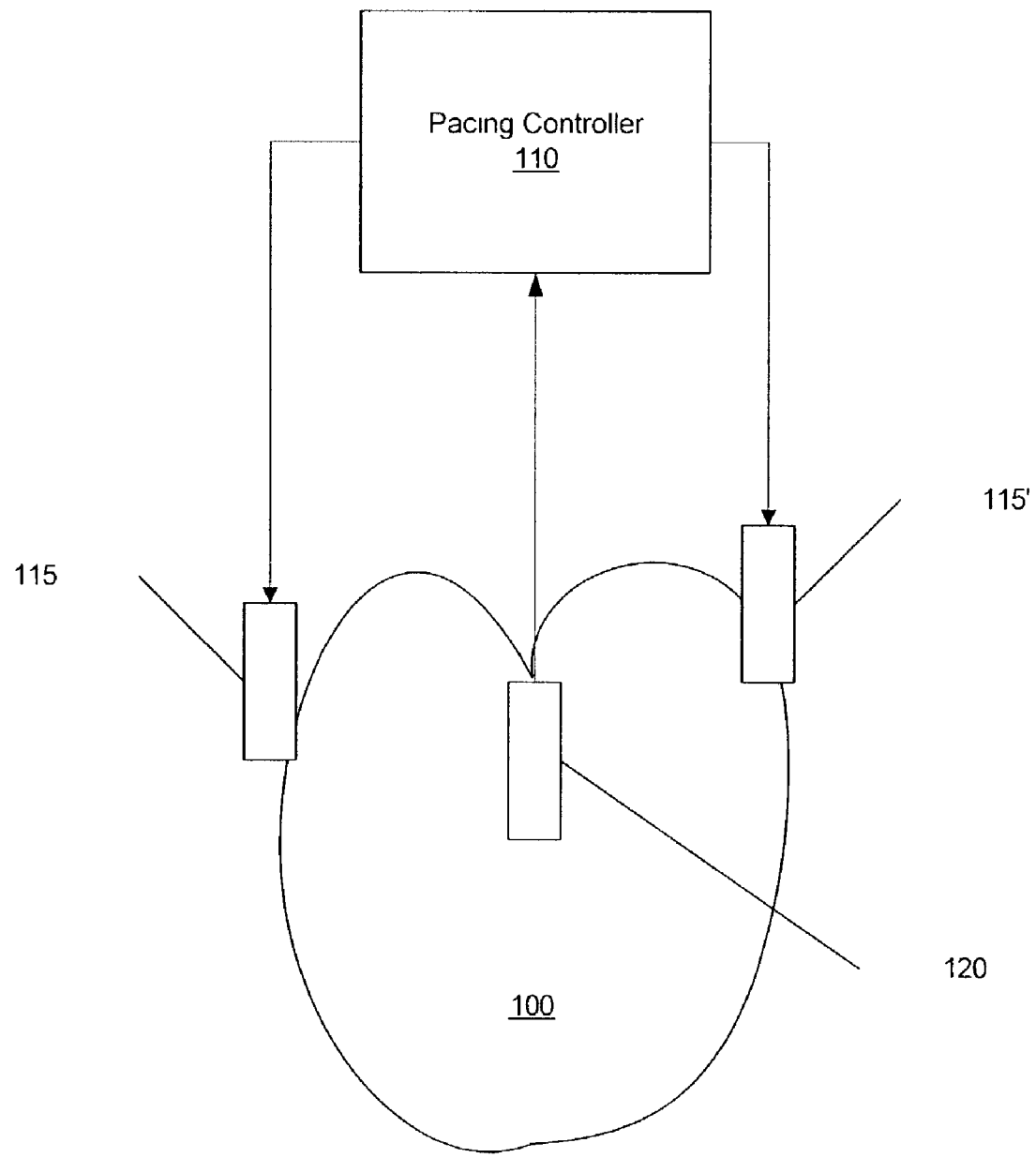
FIG. 3 is a block diagram illustrating embodiments of the present invention.

FIG. 3 is a block diagram illustrating embodiments of the present invention. As seen in FIG. 3, a pacing controller 110 has electrodes 115 and 115' that are placed in particular locations or regions of the heart 100. A sensor 120 is also provided to sense cardiac function such that the pacing controller 110 may adjust the A-V timing of stimulation provided by the first electrode 115 and/or the second electrode 115' and/or adjust the timing between stimulation of a first electrode 115 and a second electrode 115'.

The pacing controller 110 may be held on an external device (such as a remote housing which holds the operating components therein), or in a biocompatible implantable housing that holds the operating circuitry in a hermetically sealed body. The pacing controller 110 can include an electronic circuit that includes one or more amplifiers (not shown) for amplifying sensed cardiac signals and for providing stimulation to the electrodes 115 and 115'. The pacing controller 110 may also include conventional circuitry to analyze the amplified signals to detect the onset or presence of an atrial and/or ventricular arrhythmia or fibrillation condition and to identify when or if ventricular fibrillation (or other arrhythmia, depending on the specific treatment for which the device is configured) is present.

In some embodiments, the present invention can provide pacing stimulation in conjunction with a defibrillation shock pulse or pulses. As such, the pacing controller 110 can be used to time an atrial defibrillation shock pulse to provide additional assurance that defibrillation shock pulses are not delivered during sensitive portions of the cardiac cycle so as to reduce the possibility of inducing ventricular fibrillation. Ventricular sensing for timing the shocks for atrial defibrillation may be performed from the RV and/or LV electrodes used as in defibrillation devices known to those of skill in the art. See U.S. Pat. No. 5,978,704, the contents of which were incorporated by reference hereinabove. The defibrillation shock may be delivered proximate in time to the pacing stimulation (before, during, or after). Such systems are known to those of skill in the art and/or described in the above references patents and patent applications and, therefore, will not be described further herein.

In operation according to certain embodiments of the present invention, the pacing controller 110 applies a stimulation to one or more of the electrodes 115 or 115' and, after an A-V delay, applies a second stimulation to one or more of the electrodes 115 or 115'. The pacing controller 110 may also senses cardiac function utilizing the sensor 120 and adjusts the timing relationship of the first stimulation signal with respect to the second stimulation signal and/or with respect to a common reference timing, such as a spontaneous atrial signal or a pacing pulse, to improve cardiac function resulting from the application of the stimulation. In further embodiments of the present invention, the pacing controller 110 applies a first stimulation to one of the electrodes 115 or 115' and, a predefined time later, applies a second stimulation to the other of the electrodes 115 or 115'. The pacing controller 110 may also sense cardiac function utilizing the sensor 120 and adjusts the timing relationship of the first stimulation signal with respect to the second stimulation signal and/or with respect to a reference, such as an atrial signal, to improve cardiac function resulting from the application of the stimulation.

The sensed cardiac function may, for example, include sensing impedance, sensing motion and/or sensing change in distance and/or the rate of change of distance of sensors on the heart. For example, changes in impedance could be measured with a conductance catheter. Electrodes for measuring conductance could be placed on any of the leads of a device, on a body of an implantable device or on a catheter introduced just for measurement of conductance. The stimulation electrodes(s) on the left ventricle may be well suited for placement of at least one impedance measurement device. Changes in impedance and/or a rate of change of impedance may be used as an estimate of cardiac function.

Cardiac function could also be measured utilizing ultrasonic crystals positioned in at least two locations. For example, ultrasonic crystals could be positioned on two the leads of the device to measure the distance between the two leads. Crystals may be placed on the stimulation electrodes on the left ventricle and within the light ventricle. The change in distance and/or the rate of change in distance between the two leads during the heartbeat may be indicative of and/or proportional to cardiac function.

Cardiac function may also be estimated with a motion detector, such as an accelerometer. The accelerometer may be held in an implantable housing and/or on a lead, such as the electrode lead in the left ventricle. Acceleration, velocity and/or displacement and/or their derivatives and/or integrals may be related to cardiac function.

In particular embodiments of the present invention, cardiac function is directly proportional to a sensed measurement in that a maxima or minima of the sensed measurement corresponds to the maximum cardiac function improvement. In other embodiments of the present invention, maintaining a sensed measurement within a desired range provides the maximum cardiac function. Thus, changes in the sensed measurement may reflect changes in cardiac function. Alternatively, changes in cardiac function may be detected based on a combination of one or more measurements and/or further processing of one or more measurements of cardiac characteristics.

Figure 4:
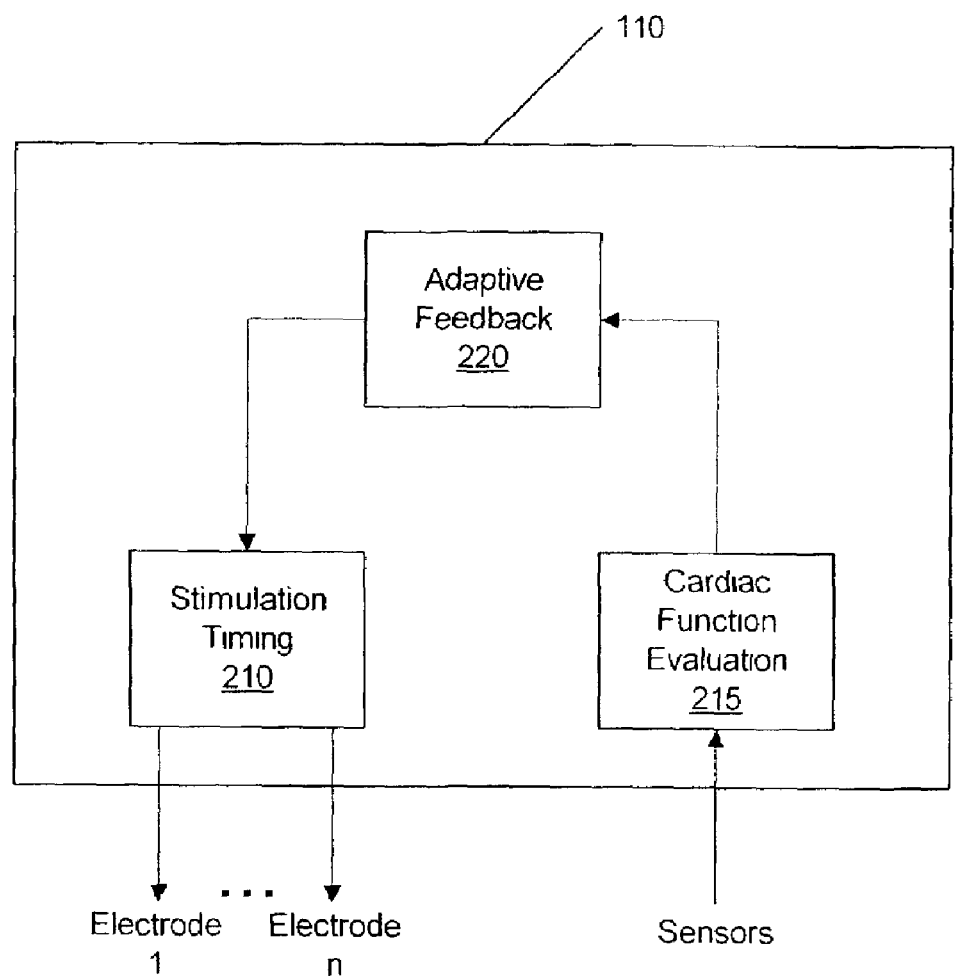
FIG. 4 is a block diagram of a pacing controller according to embodiments of the present invention.

Further embodiments of the present invention are illustrated in FIG. 4. As seen in FIG. 4, the pacing controller 110 may include a stimulation timing circuit 210 that provides stimulation to electrodes 1 through n and provides the timing of such stimulation. Electrodes 1 through n may be electrodes placed at from 2 to n stimulation sites such that a given stimulation site may have from 1 to n–1 electrodes associated therewith. A cardiac function evaluation circuit 215 receives input from one or more sensors and evaluates such input to determine a measure of cardiac function based on such input. The cardiac function evaluation circuit 215 provides the measure of cardiac function to an adaptive feedback circuit 220. The adaptive feedback circuit 220 controls the stimulation timing circuit 210 to adjust the timing of the stimulation of the electrodes 1 through n or a subset of the electrodes 1 through n relative to each other based on the measure of cardiac function.

The stimulation timing circuit 210, the cardiac function evaluation circuit 215 and the adaptive feedback circuit 220 may be in a single device or multiple devices. Furthermore, various of these circuits may be split between devices. For example, the stimulation timing circuit 210 and the adaptive feedback circuit 220 may be provided in an implantable device and the cardiac function evaluation circuit 215 provided in an external device. Other divisions of functions and/or divisions between devices may also be provided without departing from the teachings of the present invention. Accordingly, the present invention should not be construed as limited to a particular division of functions and/or division between devices but is intended to include any configuration suitable for carrying out the operations as described herein.

Figure 5:
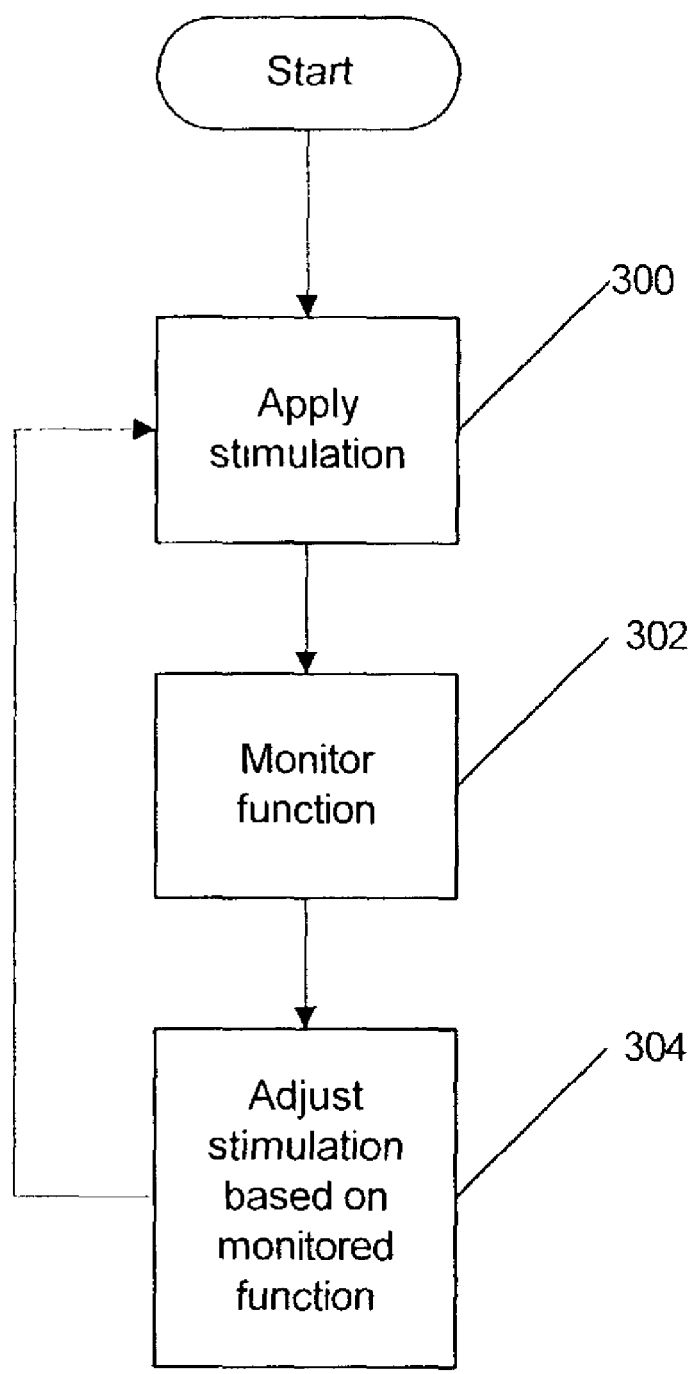
FIG. 5 is a flowchart illustrating operations according to embodiments of the present invention.

FIG. 5 is a flowchart illustrating operations according to embodiments of the present invention. As seen in FIG. 5, stimulation is applied to the heart (block 300), for example, by the stimulation timing circuit 210. The stimulation may include stimulation applied to the heart by one or more electrodes at a given cardiac timing, such as an A-V timing interval, and/or may include multiple stimulations having a predefined timing relationship between the multiple stimulations. The cardiac function resulting from application of the stimulation and/or stimulations is monitored (block 302), for example, by the cardiac function evaluation circuit 215. The cardiac timing, A-V timing interval, and/or the timing relationship of the multiple stimulations are adjusted based on the measured cardiac function (block 304). Such an adjustment(s) may be provided by the adaptive feedback circuit 220 adjusting the timing provided by the stimulation timing circuit 210 based on the measure of cardiac function provided by the cardiac function evaluation circuit 215.

Figure 6:
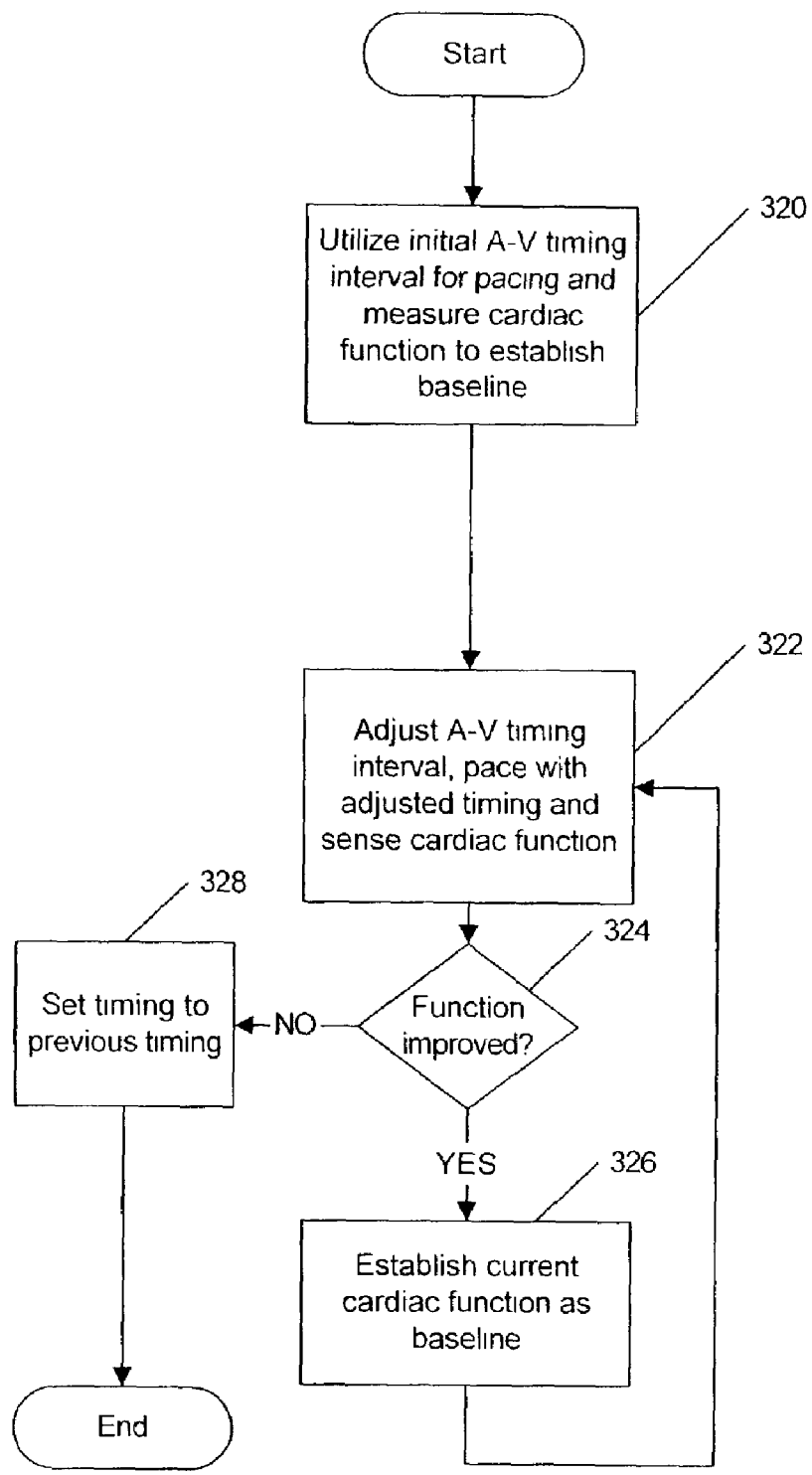
FIG. 6 is a flowchart illustrating operations according to further embodiments of the present invention.

FIG. 6 illustrates further embodiments of the present invention for adjusting a cardiac timing interval, such as an A-V timing interval. Thus, embodiments of the present invention will be described further with reference to adjusting the A-V timing interval, however, embodiments of the present invention may also be applicable to other cardiac timing intervals. As illustrated in FIG. 6, an initial A-V timing interval is utilized to provide cardiac pacing and cardiac function is measured to provide a baseline cardiac function measurement (block 320). Cardiac function may be measured as described above. This initial A-V timing interval may be a timing that is pre-established for a device and/or a patient or may be a previously established adaptive A-V timing interval utilizing techniques described herein. The A-V timing interval is adjusted, for example, by increasing or decreasing the A-V timing interval a predefined amount (block 322). Pacing is carried out using the adjusted A-V timing (block 322). Cardiac function resulting from use of the adjusted A-V timing interval is measured (block 322) and changes in cardiac function determined based on differences between the baseline cardiac function measurement and the cardiac function measurement resulting from use of the adjusted A-V timing interval. If a detected change in cardiac function indicates that cardiac function is improved over the baseline by use of the adjusted timing (block 324), the new measurement of cardiac function is established as the baseline for comparison with subsequent cardiac function measurements (block 326) and operations continue from block 322 to determine if further adjustment of the A-V timing interval will improve cardiac function If the change in timing does not result in an improvement in cardiac function (block 324), the A-V timing interval is returned to what it was prior to the adjustment of block 322 and operations for adjusting the A-V timing interval conclude (block 328). Thus, operations may continue until adjustments to the A-V timing interval no longer result in an improved value for the measure of cardiac function.

Figure 7:
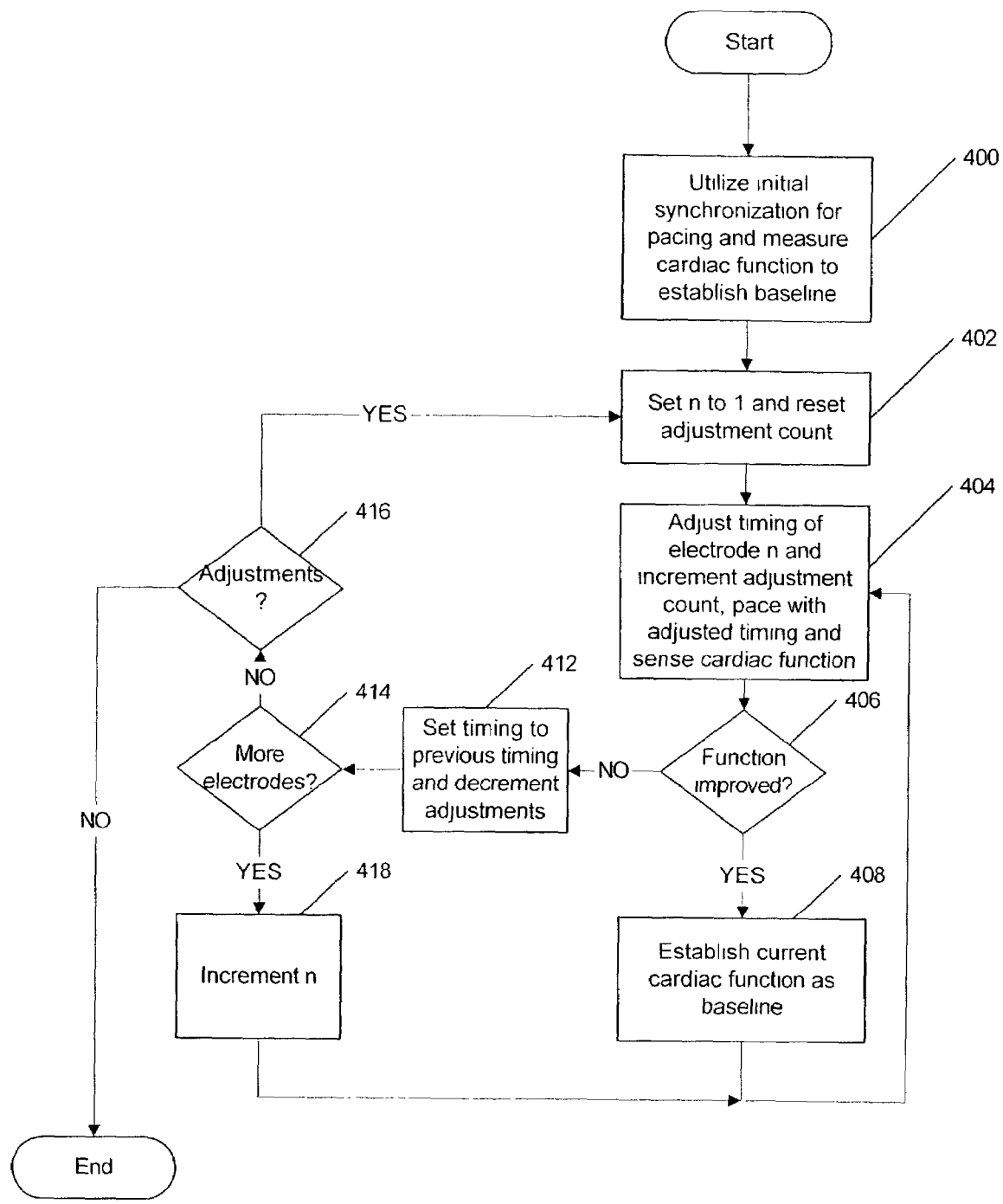
FIG. 7 is a flowchart illustrating operations according to further embodiments of the present invention.

FIG. 7 illustrates further embodiments of the present invention for establishing synchronization timings between n electrodes. As illustrated in FIG. 7, an initial synchronization timing is utilized to provide pacing utilizing biventricular synchronization and cardiac function is measured to provide a baseline cardiac function measurement (block 400). This initial synchronization timing may be a timing that is pre-established for a device and/or a patient or may be a previously established adaptive synchronization timing utilizing techniques described herein. The adjustment of the synchronization is initialized by setting a counter "n", that indicates a current electrode timing that is being adjusted, to 1 and resetting a second counter or flag that indicates whether adjustments have been made to the timing for any of the electrodes being adjusted (block 402).

The timing of stimulation by the electrode corresponding to the counter n is adjusted, for example, by delaying or advancing the stimulation of the electrode a predefined interval (block 404). The adjustment of timing may be made with respect to a common reference timing, such as a spontaneous atrial signal or a pacing signal, or with respect to other stimulations. The adjustment count is also incremented to indicate that an adjustment has been made to the timing of at least one electrode and pacing is carried out using the adjusted synchronization timing (block 404). Cardiac function resulting from use of the adjusted synchronization timing is measured (block 404) and it is determined if cardiac function is improved over the baseline by use of the adjusted timing (block 406). If cardiac function is improved (block 406), the new measurement of cardiac function is established as the baseline for comparison with subsequent cardiac function measurements (block 408) and operations continue from block 404 to determine if further adjustment of the timing associated with electrode n will improve cardiac function.

If the change in timing does not result in an improvement in cardiac function (block 406), the timing of electrode n is returned to what it was prior to the adjustment of block 404 and the adjustment count is decremented to indicate that the immediately prior adjustment of the timing for electrode n has not been carried out (block 412). If there are more electrodes for which timing is to be adjusted (block 414), then the counter n is incremented (block 418) and operations continue from block 404 to adjust the timing for the new electrode n. If all of the electrodes have been evaluated (block 414) it is determined if adjustments were made to any of the electrode timings (block 416). 953 Because the timing of the stimulation associated with one electrode may impact the timing of stimulation of other electrodes, the electrodes are again evaluated to determine if adjustments in timing would improve cardiac function by operations continuing from block 402. Thus, operations may continue until no adjustments are made to the timing of stimulation (block 416).

The operations of FIGS. 6 and/or 7 may be carried out periodically, continuously, upon initiation by an external trigger, for example, during a visit to a physician by a patient and/or upon an internally sensed event or condition. Thus, for example, the adjustment may be made every day or other fixed interval, may be repeated upon completion of a previous adjustment, may be made upon detection that cardiac function has changed, for example, by measured cardiac function falling below the baseline measurement resulting from the previous adjustment sequence, and/or by occurrence of an event, such as defibrillation or the application of an external trigger by a physician. Such an application of an external trigger may be provided, for example, by a radio frequency signal to an implantable device, a signal received over a session established with an implantable device over a telephone, a physician setting a hardware or software switch, or other such methods of generating an external signal. In other embodiments, the operations may be carried out when cardiac function decreases below a predefined threshold or percentage. Furthermore, the operations of FIGS. 6 and 7 may both be carried out. Operations for adjusting cardiac timing, A-V timing and for adjusting synchronization timing may be repeatedly carried out until additional adjustments do not improve cardiac function.

Figure 8:
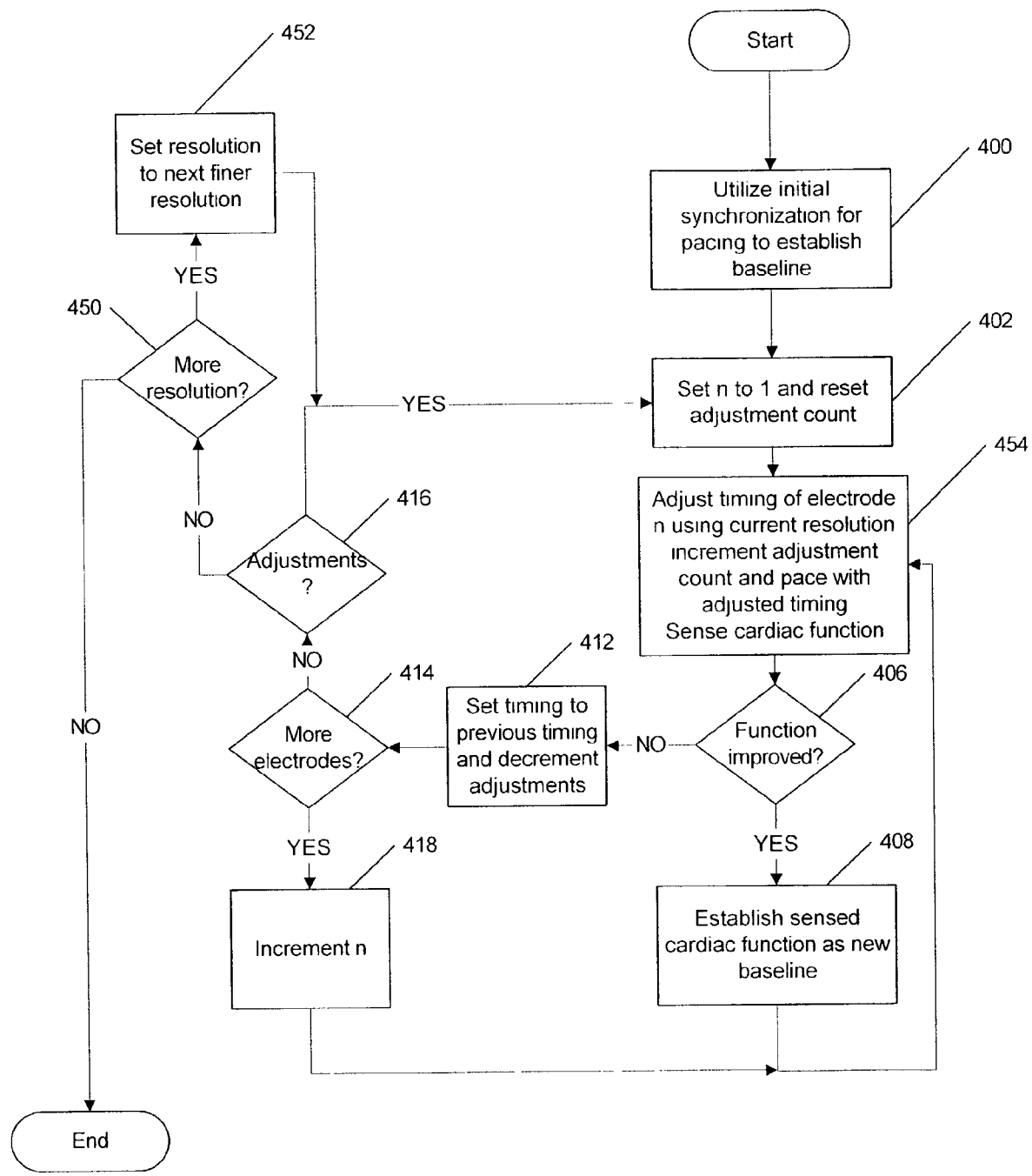
FIG. 8 is a flowchart illustrating operations according to further embodiments of the present invention.

FIG. 8 illustrates embodiments of the present invention that utilize a variable damping factor in the feedback provided by sensed cardiac function through the use of variable increments in the timing adjustments. As seen in FIG. 8, the operations of FIG. 7 are carried out to determine if an adjustment to the timing of stimulation of an electrode n improves cardiac function. However, the adjustment of the timing carried out in block 454 is provided at differing timing resolutions from, for example, a coarse resolution to a finer resolution. In certain embodiments, the finest resolution may correspond to the smallest change in timing capable of being provided by the pacing controller. In other embodiments, the finer resolution may correspond to a minimum timing interval that provides a change in cardiac function. Similarly, the coarse resolution may correspond to a maximum timing interval adjustment provided by a pacing controller and/or may correspond to a predefined proportion of a maximum allowable timing variation for a particular configuration and/or procedure of biventricular synchronization (e.g. ½ or ¼ the maximum delay between stimulations of differing electrodes). Thus, the adjustment to timing carried out in block 454 can be carried out initially utilizing a coarse resolution and, when no adjustments were made to timing utilizing the coarse resolution. If finer resolutions are available (block 450), the resolution can be set to the next finer resolution (block 452) and adjustments to timing made until no adjustments were indicated at the finer resolution. These operations may continue until a finest timing resolution was achieved (block 450).

As with the operations of FIG. 7, the operations of FIG. 8 could be carried out periodically, continuously, upon initiation by an external trigger, for example, during a visit to a physician by a patient and/or upon an internally sensed event or condition. Thus, for example, the adjustment may be made every day or other fixed interval, may be repeated upon completion of a previous adjustment, may be made upon detection that cardiac function has changed, for example, by measured cardiac function falling below the baseline measurement resulting from the previous adjustment sequence, and/or by occurrence of an event, such as defibrillation or the application of an external trigger by a physician. Furthermore, the initial resolution utilized may be adjusted such that different timing resolutions could be used as the initial timing resolution. For example, if the operations of FIG. 8 are carried out continuously, once the finest timing resolution was reached, that resolution could be used for subsequent timing adjustments. Similarly, if the operations of FIG. 8 are carried out as a result of detection of reduced cardiac function and/or the occurrence of a specific event and/or condition, the initial timing resolution could be established based on the degree of degradation in cardiac function from the baseline and/or the nature of the event and/or condition.

As will be appreciated by those of skill in the art in light of the present disclosure, FIG. 6 could also be modified in a manner similar to that illustrated in FIG. 8 to provide variable resolution adjustment of the A-V timing interval.

Additionally, the operations of FIGS. 6, 7 and/or 8 may be carried out successively where adjustments to timing are carried out by delaying the stimulation and then the operations repeated with adjustments to timing being carried out by advancing the stimulation timing. Alternatively, the stimulation timings could be advanced and then delayed. In such a manner, adjustments to timing for electrodes may be provided by delaying the timing or advancing the timing of the stimulations to provide improved cardiac function.

Similarly, different feedback mechanisms may be utilized in establishing new timing for the biventricular stimulation. For example, adjustments in timing could be made proportional to the measure of cardiac function, for example, by utilizing the difference in cardiac function before and after adjustment of stimulation timing as an error signal and adjusting the timing based on that error signal. Thus, the present invention should not be construed as limited to a particular feedback mechanism or methodology.

While embodiments of the present invention have been described in FIGS. 6, 7 and 8 with reference to adjusting timing of an electrode n, such references to an electrode n refer to one or more electrodes at a stimulation site. Thus, in some embodiments of the present invention, timing may be adjusted to multiple electrodes at a stimulation site such that electrode n refers to the electrodes associated with a particular site. In such a case, n would refer to stimulation site n and timing of stimulation of each stimulation site may be adjusted. In other embodiments of the present invention, timing adjustments may be provided for each electrode irrespective of stimulation site such that the timing of electrodes for a given stimulation site are individually adjusted. Combinations of electrode based and site based timing adjustment may also be utilized according to further embodiments of the present invention.

Furthermore, as used herein, the terms "sensing" cardiac function or "sensed" cardiac function refer to directly and/or indirectly assessing cardiac function. Such an assessment may, for example, be made by measurement of one or more cardiac characteristics and may be a direct or indirect measurement such that a surrogate or indicator of cardiac function may be measured and utilized for timing adjustment. Thus, cardiac function may not need to be expressly determined to adjust timing of the stimulations as one or more surrogates for or indicators of cardiac function may be utilized directly.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects, all generally referred to herein as a "circuit." Furthermore, the present invention may take the form of a computer program product on a computer-usable storage medium having computer-usable program code means embodied in the medium. Any suitable computer readable medium may be utilized including, a memory device, hard disks, CD-ROMs, optical storage devices, a transmission media, such as a wireless transmission media and/or those supporting the Internet or an intranet, or magnetic storage devices.

The present invention is described herein with reference to flowchart illustrations and/or block and/or flow diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block and/or flow diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

While embodiments of the present invention have been described with reference to a particular architecture and/or division of functions, the present invention should not be construed as limited to such architecture and/or division. Thus, other architectures and/or division of functions capable of carrying out the operations described herein may be utilized while still falling within the teachings of the present invention. Furthermore, while embodiments of the present invention have been described with reference to particular circuits, such circuits may include discrete components, processors, such as a microprocessor and/or signal processor, analog circuits, digital circuits and/or combinations thereof. Furthermore, embodiments of the present invention may be provided as an entirely hardware embodiment, an entirely software embodiment or combinations of hardware and software.

With regard to the operations illustrated in the flowcharts described above, as will be appreciated by those of skill in the art in light of the present disclosure, embodiments of the present invention are not limited to the specific sequence or sequences of operations described therein. Thus, for example, operations in the flowcharts may be provided out of sequence or concurrently. Similarly, other sequences of operations may be utilized while still providing the feedback adjustment according to embodiments of the present invention. Accordingly, the present invention should not be construed as limited to the particular operations or sequence of operations illustrated in the flowcharts.

Additionally, use of identifiers such as "first" and "second" are not intended to limit the invention but are provided for clarity. Furthermore, such identifiers do not imply a particular sequence or timing of events unless such sequence or timing is expressly recited. Thus, for example, a first stimulation signal may occur earlier in time than, later in time than or simultaneously with a second stimulation signal.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of pacing in a patient by biventricular synchronization, comprising:
   applying a first stimulation signal to a first region of a heart of the patient at a first time;
   applying a second stimulation signal to a second region of the heart of the patient at a second time so as to provide biventricular synchronization treatment to the heart;
   sensing cardiac function associated with application of the first and the second stimulation signals; and
   adjusting a timing relationship of application of the first stimulation signal with respect to application of the second stimulation signal based on the sensed cardiac function, wherein adjusting further comprises adjusting an A-V timing interval by a predefined interval adjustment value that is independent of the sensed cardiac function.

2. The method of claim 1, wherein the step of sensing cardiac function comprises sensing changes in impedance and wherein the step of adjusting a timing relationship comprises adjusting a timing relationship based on the sensed changes in impedance.

3. The method of claim 2, wherein the step of sensing changes in impedance comprises measuring impedance utilizing a conductance catheter positioned proximate a left ventricle of the heart of the patient.

4. The method of claim 1, wherein the step of sensing cardiac function comprises measuring changes in distance and/or the rate of change in distance between at least two locations on the heart of the patient and wherein the step of adjusting a timing relationship comprises the step of adjusting a timing relationship based on the changes in distance and/or the rate of change in distance.

5. The method of claim 4, wherein the step of measuring changes in distance and/or the rate of change in distance comprises measuring changes in distance and/or the rate of change in distance between at least an electrode positioned on a left ventricle and an electrode positioned within a right ventricle of the heart of the patient.

6. The method of claim 4, wherein the step of measuring changes in distance and/or the rate of change in distance comprises measuring changes in distance and/or the rate of change in distance utilizing ultrasonic crystals.

7. The method of claim 6, wherein the ultrasonic crystals are placed on electrodes that receive the first and the second stimulation signals.

8. The method of claim 1, wherein the step of sensing cardiac function comprises measuring motion of a location associated with the heart of the patient and wherein the step of adjusting a timing relationship comprises adjusting a timing relationship based on the measured motion.

9. The method of claim 8, wherein the location associated with the heart of the patient comprises a left ventricle of the heart of the patient.

10. The method of claim 8, wherein the step of measuring motion comprises detecting motion utilizing an accelerometer.

11. The method of claim 10, further comprising:
    determining a derivative of the detected motion; and
    estimating cardiac function based on the determined derivative.

12. The method of claim 10, further comprising:
    determining an integral of the detected motion; and
    estimating cardiac function based on the determined integral.

13. The method of claim 10, further comprising estimating cardiac function based on the detected motion and wherein the step of adjusting a timing relationship comprises adjusting a timing relationship based on the estimated cardiac function.

14. The method of claim 1, further comprising repeating applying a first stimulation signal to a heart of the patient at a first time, applying a second stimulation signal to the heart of the patient at a second time, sensing cardiac function associated with application of the first and the second stimulation and a adjusting a timing relationship of application of the first stimulation signal with respect to application of the second stimulation signal based on the sensed cardiac function until adjusting the timing relationship does not improve cardiac function.

15. The method of claim 14, wherein the step of repeating further comprises:
    adjusting timing of application of one of the first stimulation signal and the second stimulation signal until adjustment of the timing of application of the one of the first stimulation signal and the second stimulation signal does not improve cardiac function; and then
    adjusting timing of application of the other of the first stimulation signal and the second stimulation signal until adjustment of the timing of application of the other of the first stimulation signal and the second stimulation signal does not improve cardiac function.

16. The method of claim 14, further comprising:
    determining if a predefined time interval has expired; and
    carrying out the steps of applying a first stimulation, applying a second stimulation, sensing, adjusting and repeating if the predefined time interval has expired.

17. The method of claim 14, further comprising:
    determining if a change in cardiac function has occurred; and
    carrying out the steps of applying a first stimulation, applying a second stimulation, sensing, adjusting and repeating if a change in cardiac function has occurred.

18. The method of claim 14, further comprising:
    receiving an external signal initiating recalibration of biventricular synchronization timing; and
    carrying out the steps of applying a first stimulation, applying a second stimulation, sensing, adjusting and repeating responsive to receipt of the external signal.

19. The method of claim 14, wherein the step of repeating is successively repeated utilizing finer timing adjustment intervals.

20. The method of claim 1, wherein the steps of applying a first stimulation signal to a heart of the patient at a first time, applying a second stimulation signal to the heart of the patient at a second time, sensing cardiac function of the patient associated with application of the first and the second stimulation signals and adjusting a timing relationship of application of the first stimulation signal with respect to application of the second stimulation signal based on the sensed cardiac function are carried out by an implantable pacing device.

21. The method of claim 1, wherein the step of sensing cardiac function further comprises at least one of sensing heart rate of the patient and/or sensing timing and/or morphology of at least one intrinsic ventricular beat of the heart of the patient.

22. The method of claim 1, wherein the steps of sensing and adjusting are performed each time the first and second simulation signals are applied to the heart of the patient.

23. The method of claim 1, wherein the step of adjusting a timing relationship comprises delaying the second stimulation signal with respect to the first stimulation signal.

24. The method of claim 1, wherein the step of adjusting a timing relationship comprises advancing the second stimulation signal with respect to the first stimulation signal.

25. The method of claim 1, wherein the timing of the first and the second stimulation signals are established with reference to a common reference signal.

26. The method of claim 25, wherein the common reference signal comprises a spontaneous atrial signal.

27. The method of claim 1, further comprising the steps of:
applying stimulation to a heart of the patient utilizing the A-V timing interval;
detecting a change in cardiac function by sensing cardiac function associated with application of the stimulation using the A-V timing interval; and
adjusting the A-V timing interval based on the detected change in cardiac function.

28. The method of claim 27, further comprising the step of repeating applying stimulation to a heart of the patient utilizing the A-V timing interval, detecting a change in cardiac function by sensing cardiac function associated with application of the stimulation using the A-V timing interval and adjusting the A-V timing interval based on the detected change in cardiac function until the sensed cardiac function does not indicate an improvement in cardiac function.

29. A method of pacing in a patient by biventricular synchronization, comprising:
applying a first stimulation signal to a first region of a heart of the patient at a first time;
applying a second stimulation signal to a second region of the heart of the patient at a second time so as to provide biventricular synchronization treatment to the heart;
sensing cardiac function associated with application of the first and the second stimulation signals;
adjusting a timing relationship of application of the first stimulation signal with respect to application of the second stimulation signal based on the sensed cardiac function;
applying stimulation to a heart of the patient utilizing an A-V timing interval;
detecting a change in cardiac function by sensing cardiac function associated with application of the stimulation using the A-V timing interval;
adjusting the A-V timing interval based on the detected change in cardiac function; and
repeating applying stimulation to a heart of the patient utilizing an A-V timing interval, detecting a change in cardiac function by sensing cardiac function associated with application of the stimulation using the A-V timing interval and adjusting the A-V timing interval based on the detected change in cardiac function until the sensed cardiac function does not indicate an improvement in cardiac function, wherein the step of adjusting the A-V timing interval comprises adjusting the A-V timing interval by a predefined interval adjustment value that is independent of the sensed cardiac function.

30. A cardiac pacing system utilizing biventricular synchronization, comprising:
an electrode stimulation timing circuit configured to control timing between application of stimulation to a first electrode and application of stimulation to a second electrode to provide biventricular synchronization;
a cardiac function sensing circuit; and
a feedback control circuit operatively associated with the electrode stimulation timing circuit and the cardiac function sensing circuit and configured to adjust the timing of application of stimulation to the first electrode and application of stimulation to the second electrode based on sensed cardiac function;
wherein the feedback control circuit is further configured to adjust an A-V timing interval by a predefined interval adjustment value that is independent of the sensed cardiac function.

31. The system of claim 30, wherein the cardiac function sensing circuit is configured to sense changes in impedance of at least one region of the heart.

32. The system of claim 31, further comprising a conductance catheter configured to be positioned on a left ventricle of the heart of the patient and wherein the cardiac function sensing circuit is operably associated with the conductance catheter.

33. The system of claim 30, wherein the cardiac function sensing circuit is configured to measure changes in distance and/or the rate of change in distance between at least two locations on the heart of the patient.

34. The system of claim 33, wherein cardiac function sensing circuit is further configured to measure changes in distance and/or the rate of change in distance between at least an electrode positioned on a left ventricle and an electrode positioned within a right ventricle of the heart of the patient.

35. The system of claim 33, further comprising ultrasonic crystals positioned on the first electrode and the second electrode and wherein the cardiac function sensing circuit is further configured to measure changes in distance and/or the rate of change in distance utilizing the ultrasonic crystals.

36. The system of claim 30, wherein the cardiac function sensing circuit is configured to measure motion of a location associated with the heart of the patient.

37. The system of claim 36, wherein the location associated with the heart of the patient comprises proximate a left ventricle of the heart of the patient.

38. The system of claim 36, wherein the cardiac function sensing circuit is further configured to detect motion utilizing an accelerometer.

39. The system of claim 38, wherein the cardiac function sensing circuit is further configured to determine a derivative of the detected motion and estimate cardiac function based on t0 he determined derivative.

40. The system of claim 38, wherein the cardiac function sensing circuit is further configured to estimate cardiac function based on the detected motion.

41. The system of claim 30, wherein the timing circuit, sensing circuit and feedback circuit are further configured to repeatedly apply a first stimulation to a heart of the patient at a first time, apply a second stimulation to the heart of the patient at a second time, sense cardiac function of the patient resulting from application of the first and the second stimulation and adjust timing of the first stimulation and/or the second stimulation based on the sensed cardiac function until adjusting timing does not improve cardiac function.

42. The system of claim 41, wherein the timing circuit, sensing circuit and feedback circuit are further configured to repeat adjust timing between stimulation of the first electrode and stimulation of the second electrode after a predefined time interval has elapsed.

43. The system of claim 41, wherein the sensing circuit is further configured to determine if a change in cardiac function has occurred; and
wherein the timing circuit, sensing circuit and feedback circuit are further configured to adjust the timing between stimulation of the first electrode and stimulation of the second electrode if a change in cardiac function has occurred.

44. The system of claim 41, wherein the feedback circuit is further configured to receive en external signal initiating recalibration of biventricular synchronization timing; and
wherein the timing circuit, sensing circuit and feedback circuit are further configured to adjust the timing between stimulation of the first electrode and stimulation of the second electrode responsive to receipt of the external signal.

45. The system of claim 30, wherein the timing circuit, sensing circuit and feedback circuit are further configured to adjust timing of one of the first stimulation and the second stimulation until adjustment of timing of the one of the first stimulation and the second stimulation does not improve cardiac function and then adjust timing of the other of the first stimulation and the second stimulation until adjustment of timing of the other of the first stimulation and the second stimulation does not improve cardiac function.

46. The system of claim 30, wherein the electrode stimulation timing circuit is further configured to provide cardiac stimulation at the A-V timing interval; and
wherein the feedback control circuit is further configured to adjust the A-V timing interval based on a change in the sensed cardiac function.

47. The system of claim 30, wherein the sensing circuit is configured to sense cardiac function each time the first and second simulations are applied to the heart of the patient and wherein the feedback circuit is configured to adjust timing each time the first and second simulations are applied to the heart of the patient.

48. The system of claim 30, wherein the timing circuit, the sensing circuit and/or the feedback circuit comprise an implantable pacing device.

49. The system of claim 30, wherein the cardiac function sensing circuit is further configured to sense heart rate of the patient and/or timing and/or morphology of at least one intrinsic ventricular beat of the heart of the patient.

50. The system of claim 30, wherein the feedback circuit adjusts timing of stimulation of the first electrode with respect to stimulation of the second electrode proportional to the sensed cardiac function.

51. The system of claim 30, wherein the timing control circuit adjusts timing by delaying the second stimulation with respect to the first stimulation.

52. The system of claim 30, wherein the timing control circuit adjusts timing by advancing the second stimulation with respect to the first stimulation.

53. The system of claim 30, wherein the timing control circuit adjusts timing of the first and the second stimulation signals with reference to a common reference signal.

54. The system of claim 53, wherein the common reference signal comprises a spontaneous atrial signal.

55. A cardiac pacing system utilizing biventricular synchronization, comprising:
an electrode stimulation timing circuit configured to control timing between application of stimulation to a first electrode and application of stimulation to a second electrode to provide biventricular synchronization;
a cardiac function sensing circuit; and
a feedback control circuit operatively associated with the electrode stimulation timing circuit and the cardiac function sensing circuit and configured to adjust the timing of application of stimulation to the first electrode and application of stimulation to the second electrode based on sensed cardiac function;
wherein the cardiac function sensing circuit is configured to measure motion of a location associated with the heart of the patient;
wherein the cardiac function sensing circuit is further configured to detect motion utilizing an accelerometer; and
wherein the cardiac function sensing circuit is further configured to determine an integral of the detected motion and estimate cardiac function based on the determined integral.

56. The system of claim 55, wherein the timing circuit is configured to adjust the timing between the stimulation of the first electrode and the stimulation of the second electrode utilizing variable timing adjustment intervals.

57. A system for cardiac pacing in a patient by biventricular synchronization, comprising:
means for applying a first stimulation signal to a first region of a heart of the patient at a first time;
means for applying a second stimulation signal to a second region of the heart of the patient at a second time so as to provide biventricular synchronization treatment to the heart;
means for sensing cardiac function associated with application of the first and the second stimulation signals; and
means for adjusting a timing relationship of application of the first stimulation signal with respect to application of the second stimulation signal based on the sensed cardiac function, wherein the means for adjusting further comprises means for adjusting an A-V timing interval by a predefined interval adjustment value that is independent of the sensed cardiac function.

58. The system of claim 57, wherein the means for adjusting timing comprises means for advancing the second stimulation signal with respect to the first stimulation signal.

59. The system of claim 57, wherein the means for sensing cardiac function comprises means for sensing changes in impedance.

60. The system of claim 59, wherein the means for sensing changes in impedance comprises measuring impedance utilizing a conductance catheter positioned on a left ventricle of the heart of the patient.

61. The system of claim 57, wherein the means for sensing cardiac function comprises means for measuring changes in distance and/or the rate of change in distance between at least two locations on the heart of the patient.

62. The system of claim 61, wherein the means for measuring changes in distance and/or the rate of change in distance comprises means for measuring changes in distance and/or the rate of change in distance between at least an electrode positioned proximate a left ventricle and an electrode positioned within a right ventricle of the heart of the patient.

63. The system of claim 61, wherein the means for measuring changes in distance and/or the rate of change in distance comprises means for measuring changes in distance and/or the rate of change in distance utilizing ultrasonic crystals.

64. The system of claim 63, wherein the ultrasonic crystals are placed on electrodes the first and the second electrodes.

65. The system of claim 57, wherein the means for sensing cardiac function comprises means for measuring motion of a location associated with the heart of the patient.

66. The system of claim 65, wherein the location associated with the heart of the patient comprises a left ventricle of the heart of the patient.

67. The system of claim 65, wherein the means for measuring motion comprises an accelerometer.

68. The system of claim 67, wherein the means for sensing further comprise means for estimating cardiac function based on the detected motion.

69. The system of claim 65, further comprising:
means for determining an integral of the detected motion; and
means for estimating cardiac function based on the determined integral.

70. The system of claim 65, further comprising:
means for determining a derivative of the detected motion; and
means for estimating cardiac function based on the determined derivative.

71. The system of claim 57, further comprising means for repeatedly applying a first stimulation signal to a heart of the patient at a first time, applying a second stimulation signal to the heart of the patient at a second time, sensing cardiac function of the patient associated with application of the first and the second stimulation and adjusting a timing relationship until adjusting timing does not improve cardiac function.

72. The system of claim 71, wherein the means for repeatedly applying further comprises:
means for adjusting timing of one of the first stimulation signal and the second stimulation signal until adjustment of timing of the one of the first stimulation signal and the second stimulation signal does not improve cardiac function and then adjusting timing of the other of the first stimulation signal and the second stimulation signal until adjustment of timing of the other of the first stimulation signal and the second stimulation signal does not improve cardiac function.

73. The system of claim 71, further comprising:
means for determining if a predefined time interval has expired; and
wherein the means for repeatedly applying is responsive to the means for determining if a predetermined time interval has expired.

74. The system of claim 71, further comprising:
means for determining if a change in cardiac function has occurred; and
wherein the means for repeatedly applying is responsive to the means for determining if a change in cardiac function has occurred.

75. The system of claim 71, further comprising:
means for receiving an external signal initiating recalibration of biventricular synchronization timing; and
wherein the means for repeatedly applying is responsive to the means for receiving an external signal.

76. The system of claim 71, wherein the means for adjusting timing utilizes successively finer timing adjustment intervals.

77. The system of claim 57, wherein the means for applying a first stimulation signal to a heart of the patient at a first time, the means for applying a second stimulation signal to the heart of the patient at a second time, the means for sensing cardiac function of the patient associated with application of the first and the second stimulation and/or the means for adjusting a timing relationship comprise an implantable pacing device.

78. The system of claim 57, wherein the means for sensing cardiac function further comprises means for sensing a heart rate of the patient and/or sensing timing and/or morphology of at least one intrinsic ventricular beat of the heart of the patient.

79. The system of claim 57, wherein the means for sensing and means for adjusting are responsive to each application of the first and second simulation signals to the heart.

80. The system of claim 57, wherein the means for adjusting timing comprises means for delaying the second stimulation signal with respect to the first stimulation signal.

81. The system of claim 57, wherein the means for adjusting timing comprises means for adjusting timing of the first and the second stimulation signals with reference to a common reference signal.

82. The system of claim 81, wherein the common reference signal comprises a spontaneous atrial signal.

83. A system for cardiac pacing in a patient by biventricular synchronization, comprising:
means for applying a first stimulation signal to a first region of a heart of the patient at a first time;
means for applying a second stimulation signal to a second region of the heart of the patient at a second time so as to provide biventricular synchronization treatment to the heart;
means for sensing cardiac function associated with application of the first and the second stimulation signals;
means for adjusting a timing relationship of application of the first stimulation signal with respect to application of the second stimulation signal based on the sensed cardiac function;
means for applying stimulation to a heart of the patient utilizing an A-V timing interval;
means for detecting a change in cardiac function by sensing cardiac function associated with application of the stimulation using the A-V timing interval; and
means for adjusting the A-V timing interval based on the detected change in cardiac function, wherein the means for adjusting the A-V timing interval comprises means for adjusting the A-V timing interval by a predefined interval adjustment value that is independent of the sensed cardiac function.

* * * * *

UNITED STATES PATENT AND TRADEMARK OFFICE
CERTIFICATE OF CORRECTION

PATENT NO. : 7,139,608 B2 Page 1 of 1
APPLICATION NO. : 10/210587
DATED : November 21, 2006
INVENTOR(S) : Ideker et al.

It is certified that error appears in the above-identified patent and that said Letters Patent is hereby corrected as shown below:

<u>Column 20,</u>

Line 53: Pleae correct "based on t0 he" To read --based on the--

Signed and Sealed this

Fifteenth Day of May, 2007

JON W. DUDAS
*Director of the United States Patent and Trademark Office*